(12) United States Patent
Singer et al.

(10) Patent No.: US 8,591,872 B2
(45) Date of Patent: Nov. 26, 2013

(54) COMPOSITION AND PROCESS FOR REDUCING THE CURL AND FRIZZINESS OF HAIR

(75) Inventors: Jim Singer, South Orange, NJ (US); Christine Shin, North Brunswick, NJ (US); Sudarat Infahseng, Jersey City, NJ (US); Xiang Zhu, Manalapan, NJ (US); Clarissa Nogueira, Hoboken, NJ (US)

(73) Assignee: L'Oreal, Paris (FR)

( * ) Notice: Subject to any disclaimer, the term of this patent is extended or adjusted under 35 U.S.C. 154(b) by 37 days.

(21) Appl. No.: 13/340,930

(22) Filed: Dec. 30, 2011

(65) Prior Publication Data
US 2013/0167860 A1    Jul. 4, 2013

(51) Int. Cl.
*A61Q 5/00*    (2006.01)
(52) U.S. Cl.
USPC ........................................ 424/70.12; 514/588
(58) Field of Classification Search
None
See application file for complete search history.

(56) References Cited

U.S. PATENT DOCUMENTS

| | | | |
|---|---|---|---|
| 4,507,278 A | 3/1985 | DeMarco et al. | |
| 4,698,065 A | 10/1987 | Hoeffkes et al. | |
| 4,844,711 A | 7/1989 | Hoppe et al. | |
| 5,160,730 A | 11/1992 | Dubief et al. | |
| 5,180,584 A | 1/1993 | Sebag et al. | |
| 5,275,755 A | 1/1994 | Sebag et al. | |
| 5,637,306 A | 6/1997 | Cauwet et al. | |
| 5,879,414 A | 3/1999 | Milazzo | |
| 6,306,182 B1 | 10/2001 | Chan et al. | |
| 6,352,699 B1 | 3/2002 | Mondet et al. | |
| 6,368,584 B1 | 4/2002 | Garnier et al. | |
| 6,551,361 B1 | 4/2003 | Cornwell et al. | |
| 6,607,713 B1 | 8/2003 | Chodorowski et al. | |
| 6,737,047 B2 * | 5/2004 | Jeanne-Rose et al. | 424/61 |
| 6,953,572 B1 | 10/2005 | Samain et al. | |
| 6,953,584 B1 | 10/2005 | Samain et al. | |
| 7,037,347 B2 | 5/2006 | Kuzuhara et al. | |
| 7,122,062 B2 | 10/2006 | Yamashita et al. | |
| 7,176,170 B2 | 2/2007 | Dubief et al. | |
| 7,223,384 B1 | 5/2007 | Decoster et al. | |
| 7,244,420 B1 | 7/2007 | Samain et al. | |
| 7,740,664 B2 | 6/2010 | Benabdillah | |
| 7,799,093 B2 | 9/2010 | Brun et al. | |
| 7,905,927 B2 | 3/2011 | Hercouet | |
| 7,909,889 B2 | 3/2011 | Charrier et al. | |
| 7,909,892 B2 | 3/2011 | Lautenbach et al. | |
| 7,959,687 B2 | 6/2011 | Charrier et al. | |
| 2002/0041856 A1 | 4/2002 | Jeanne-Rose et al. | |
| 2004/0013632 A1 | 1/2004 | Giroud et al. | |
| 2004/0045099 A1 | 3/2004 | Kuzuhara et al. | |
| 2004/0185020 A1 | 9/2004 | Gawtrey et al. | |
| 2005/0071932 A1 | 4/2005 | Lautenbach et al. | |
| 2005/0100523 A1 | 5/2005 | Maubru et al. | |
| 2006/0127337 A1 * | 6/2006 | Radisson | 424/70.2 |
| 2008/0226576 A1 | 9/2008 | Benabdillah et al. | |
| 2009/0183320 A1 | 7/2009 | Benabdillah | |
| 2009/0291058 A1 | 11/2009 | Woodland et al. | |
| 2009/0293899 A1 | 12/2009 | Woodland et al. | |
| 2010/0254932 A1 | 10/2010 | Benabdillah et al. | |
| 2010/0297049 A1 | 11/2010 | Samain et al. | |
| 2011/0052520 A1 | 3/2011 | Nguyen et al. | |
| 2011/0158927 A1 | 6/2011 | Viravau et al. | |

FOREIGN PATENT DOCUMENTS

| | | |
|---|---|---|
| CN | 101069673 A | 11/2007 |
| CN | 101069673 A | 11/2007 |
| DE | 102006026009 A1 | 12/2007 |
| EP | 0560682 | 9/1993 |
| EP | 1216022 A1 | 6/2002 |
| EP | 1216023 A1 | 6/2002 |
| EP | 1221929 A1 | 7/2002 |
| EP | 1510197 A1 | 3/2005 |
| EP | 1862198 A2 | 12/2007 |
| EP | 1889602 | 2/2008 |
| EP | 1944062 | 7/2008 |
| FR | 2789896 A1 | 8/2000 |
| FR | 1207842 A1 | 5/2002 |
| FR | 2836633 A1 | 9/2003 |
| FR | 2838960 A1 | 10/2003 |
| FR | 2910276 | 6/2008 |
| FR | 2922759 A1 | 5/2009 |
| FR | 2926984 | 8/2009 |
| FR | 2929112 A1 | 10/2009 |
| FR | 2944963 A1 | 11/2010 |
| FR | 2944964 A1 | 11/2010 |
| FR | 2944966 A1 | 11/2010 |
| FR | 2950531 | 4/2011 |
| JP | 60004116 A | 1/1985 |
| JP | 7330556 A | 12/1995 |
| JP | 9175960 A | 7/1997 |
| JP | 9278636 A | 10/1997 |

(Continued)

OTHER PUBLICATIONS

U.S. Appl. No. 61/581,769, filed Dec. 30, 2011, Jim Singer et al.

(Continued)

*Primary Examiner* — Jyothsna Venkat
(74) *Attorney, Agent, or Firm* — L'Oreal USA

(57) ABSTRACT

A process for reducing curl and/or frizziness of hair comprising: (a) providing a composition for reducing curl and/or frizziness of hair, said composition comprising, in a cosmetically acceptable carrier: (i) at least one non-hydroxide base; (ii) at least one protein denaturant different from (a)(i); (iii) at least one alkoxysilane comprising at least one solubilizing functional group; and (iv) optionally, at least one fatty substance; (b) contacting the hair with the composition in (a) to form treated hair; (c) optionally, rinsing the composition in (a) from the treated hair; (d) optionally, contacting the treated hair with a conditioning agent; (e) smoothing the treated hair using a combination of heat and means for physically smoothing hair to form smoothed hair; (f) optionally, shampooing the smoothed hair; and (g) rinsing the smoothed hair.

15 Claims, No Drawings

(56) References Cited

FOREIGN PATENT DOCUMENTS

| | | | |
|---|---|---|---|
| JP | 9278636 A | 10/1997 | |
| JP | 2001220322 A | 8/2001 | |
| JP | 3686352 B2 | 11/2002 | |
| JP | 2002326916 A | 11/2002 | |
| JP | 2003128527 A | 5/2003 | |
| JP | 2004217672 A | 8/2004 | |
| JP | 2008273869 A | 11/2008 | |
| WO | WO 99/60993 | 12/1999 | |
| WO | WO 0048557 | 8/2000 | |
| WO | WO 2006/018198 A1 | 2/2006 | |
| WO | WO 2008/020730 A1 | 2/2008 | |
| WO | WO 2009/117344 | * | 9/2009 |
| WO | WO 2011/052520 A1 | 5/2011 | |
| WO | WO 2011/073279 | 6/2011 | |
| WO | WO 2011/073578 | 6/2011 | |
| WO | WO 2011/074144 | 6/2011 | |
| WO | WO 2011/089985 | 7/2011 | |

OTHER PUBLICATIONS

U.S. Appl. No. 09/055,760, filed Dec. 19, 2000, L'Oreal.
"Chemistry and Technology of Silicones" (1968), Walter Noll—Academic Press.
"Volatile Silicone Fluids for Cosmetics" (Jan. 1976, vol. 1, pp. 29-32), Todd Byers—Cosmetics and Toiletries.

* cited by examiner

COMPOSITION AND PROCESS FOR REDUCING THE CURL AND FRIZZINESS OF HAIR

FIELD OF THE INVENTION

The present invention is directed to a novel composition and process employing an alkoxysilane for use in hair manageability applications for reducing the curl and/or frizziness of hair.

BACKGROUND OF THE INVENTION

Hair products for reducing the curl and frizziness of hair have been commercially available for over fifty years for people who want less curly and more manageable hair. Such products are also known as hair straightening or relaxing products and are generally composed of a strong hydroxide base compound that breaks the bonds in the hair in order to straighten or relax curly/kinky hair. There are primarily four different types of alkaline metal hydroxide hair straighteners in use: calcium hydroxide, lithium hydroxide, sodium hydroxide, and potassium hydroxide. The straightening or relaxing product is usually applied quickly and can only remain on the hair for a very limited amount of time because the alkalinity of such products, if not rinsed from the hair at the appropriate time, can damage the hair, as well as cause chemical burns to the scalp and areas surrounding the hair.

Other straightening or relaxing formulations use guanidinium hydroxide which can be formed from the reaction of guanidine carbonate and a very small amount of soluble hydroxide such as calcium hydroxide. The reaction between these two compounds leads to the formation of guanidinium hydroxide and calcium carbonate, which precipitates in the composition. While such a system may provide a better relaxing efficacy and better skin tolerance, the calcium carbonate precipitate makes the final rinsing of the hair much more difficult, and leaves on the hair and the scalp, mineral particles that give the hair a coarse feel and an unattractive appearance resembling dandruff.

Another known permanent hair straightener or reshaping technology employs reducing agents such as thighlycolic acid and cysteine technologies as well as non thiol-based reducing agents such as sulfites and bisulfites which permanently reduce hair bonds. Still other hair relaxing or straightening compositions and processes involve the use of protein denaturants in combination with heat. Protein denaturants are compounds which cause a reversible unfolding of a protein. However, many of the proposed compositions contain formalin, formalin derivatives or formaldehyde-generating compounds, which are known to break down to formaldehyde with high heat, such as during flat ironing of the hair. Formaldehyde fumes generated owing to the break down have been found to cause headaches, respiratory, eye, and mucous membrane irritations, respiratory illnesses, cancer, or even death. Thus, these compositions pose significant safety concerns.

In order to address the concerns mentioned above, other compositions and processes have been proposed, such as those that involve the application of compositions containing non-hydroxide bases and/or protein denaturants that are of the non-formalin or non-formalin derivative types or which do not generate formaldehyde, including pre-washing the hair with high pH compositions. However, there still exists a need to improve such methods and compositions that are just as safe, and which are able to provide greater and longer lasting curl pattern reduction and frizz control, more effective straightening of hair, increased manageability of hair, while minimizing damage to the hair. At the same time, less hair treatment or processing times to achieve these attributes are highly desirable.

Thus, there is an ongoing need and desire to provide a composition and process for effectively straightening or reducing the curl and/or frizziness of hair in an efficient and safe manner while imparting other cosmetic and functional benefits to the hair.

BRIEF SUMMARY OF THE INVENTION

The present invention is directed to a process for reducing curl and/or frizziness of hair comprising:
 (a) providing a composition for reducing curl and/or frizziness of hair, said composition comprising, in a cosmetically acceptable carrier:
  (i) at least one non-hydroxide base;
  (ii) at least one protein denaturant different from (a)(i);
  (iii) at least one alkoxysilane comprising at least one solubilizing functional group; and
  (iv) optionally, at least one fatty substance;
 (b) contacting the hair with the composition in (a) to form treated hair;
 (c) optionally, rinsing the composition in (a) from the treated hair;
 (d) optionally, contacting the treated hair with a conditioning agent;
 (e) smoothing the treated hair using a combination of heat and means for physically smoothing hair to form smoothed hair;
 (f) optionally, shampooing the smoothed hair; and
 (g) rinsing the smoothed hair.

The present invention is also directed to a composition for reducing curl and/or frizziness of hair, said composition comprising, in a cosmetically acceptable carrier:
 (a) from about 0.1% to about 50% by weight of at least one non-hydroxide base;
 (b) from about 0.1% to about 50% by weight of at least one protein denaturant different from (a);
 (c) at least one alkoxysilane comprising at least one solubilizing functional group; and
 (d) optionally, at least one fatty substance,
all weights based on the weight of the composition.

It has been surprisingly and unexpectedly discovered that the use of the above-disclosed compositions and process deliver a significant and longer lasting reduction in hair curl pattern or configuration and significant frizz control, while requiring less processing times and imparting significant benefits to the hair, including increased hair manageability, retention of hair curl reduction and hair volume reduction even with successive washings, and retention of the color of artificially dyed hair.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

As used herein, the term "hair" is meant to include keratinous fibers. As used, the term "hair" may include "living" hair, i.e. on a living body, or may be "non-living" i.e. in a wig, hairpiece or other aggregation of non-living fibers, such as though used in textiles and fabrics. Mammalian hair, e.g. human hair, is preferred in various embodiments. However wool, fur and other melanin-containing fibers are suitable for use in the methods and with the compositions described herein.

The term "anhydrous" as used herein is intended to mean that the composition is either completely free of unbound water or contains substantially no unbound water, such as, for example, no more than about 1% by weight, such as no more than about 0.5% by weight, based on the weight of each composition.

As used herein, the phrase "salts and derivatives thereof" is intended to mean all salts and derivatives comprising the same functional structure as the compound they are referring to, and that have similar properties.

As used herein, the phrase "minimizing damage" to the hair and/or skin is intended to mean that the breakage of the hair has been reduced or eliminated.

As used herein, the term "ready-to-use composition" means a composition intended to be applied in unmodified form to the keratin fibers, i.e. it may be stored in unmodified form before use or may result from the extemporaneous mixing of two or more compositions.

As used herein, the term "applying" a composition to the hair or "treating" the hair with a composition is intended to mean contacting the hair with at least one of the compositions of the invention, in any manner.

As used herein, the terms "reducing the curl or frizziness of the hair" and their variations as used herein broadly means any of the following: reducing the hair's curl configuration (or pattern), or reducing the degree of curl of hair to make it more straight, or changing the shape of hair, or reducing the frizziness of hair (or reducing the volume of the head of hair), or straightening or relaxing the hair, for a period of time, permanently and/or temporarily.

As used herein, the step of "smoothing the treated hair using a combination of heat and means for physically smoothing hair" as described herein means simultaneously using heat and means for physically smoothing hair.

As used herein, "cosmetically acceptable" means that the item in question is compatible with any human keratin material and in particular human keratinous fibers, such as human hair.

As used herein, "cosmetically acceptable carrier" means a carrier that is compatible with any human keratin material and in particular human keratinous fibers, such as human hair.

As used herein, "conditioning" means imparting to at least one keratinous fiber at least one property chosen from combability, manageability, moisture-retentivity, luster, shine, and softness. In case of combing, the level of conditioning is evaluated by measuring, and comparing, the ease of combability of the treated hair and of the untreated hair in terms of combing work (gm-in).

As used herein, "formed from," means obtained from chemical reaction of, wherein "chemical reaction," includes spontaneous chemical reactions and induced chemical reactions. As used herein, the phrase "formed from", is open ended and does not limit the components of the composition to those listed.

As used herein, the term "rheology-modifying agent" or "rheology modifier" means any compound capable of giving a viscosity to the oxidizing composition such that, once it is applied onto hair, this composition does not run, and remains perfectly localized at the point of application.

As used herein, the methods and compositions disclosed may be used on the hair that has not been artificially dyed or pigmented.

As used herein, the methods and compositions disclosed may be also used on the hair that has been artificially dyed or pigmented.

The methods and compositions disclosed are also used to reduce the frizziness of hair and/or improve the condition of the hair or keep hair conditioned. When the amount of moisture in hair decreases due to weather conditions or exposure to high temperatures during styling processes, the hair gives up surface electrons more readily and develops a positive electrostatic charge. The positive charge of individual hair fibers causes the hair fibers to repel one another resulting in a "static flyaway" condition (i.e., frizzy hair). Loss of moisture in the hair also causes hair to become brittle and damaged resulting in less shiny and more unattractive hair. Hair is often exposed to dry weather conditions in arid regions and/or during the winter months. Furthermore, many styling processes utilize heat to drive out moisture in the hair in order to lock in a temporary style that persists until the hair reabsorbs moisture.

Alkoxysilanes are not typically used in formulating cosmetic products/personal care products. In particular, alkoxysilanes are not usually employed in hair products, including manageability products for reducing curl and frizz. However, alkoxysilanes, particularly those with at least one solubilizing functional group can attract water molecules, thereby causing a gelling effect when exposed to the water. Without intending to be bound by theory, the use of alkoxysilanes is believed to help with reducing the adverse effects of the use of heat on the hair which would tend to reduce the moisture of the hair, thereby resulting in unattractive and dry hair.

Thus, it was surprisingly and unexpectedly found that the combination of at least one alkoxysilane with at least one non-hydroxide base, at least one protein denaturant, and a combination of heat and means for physically smoothing hair results in a composition that significantly improved curl reducing and frizz reducing capabilities that are longer lasting, typically up to three to four months, particularly when compared to the effect of compositions without the alkoxysilane with respect to the same attributes. It is also believed that the alkoxysilane attaches to the hair fiber shaft to fill in the shaft and impart strength to the hair fibers.

Without intending to be bound by theory, it is believed that the present invention's composition results in a unique synergy between the non-hydroxide base, protein denaturant, and the alkoxysilane. It is also believed that these synergies translate into overall improved curl reduction/hair straightening and improved frizz/hair volume reduction which is maintained for long periods of time and after multiple washings.

Once again, without intending to be bound by theory, it is also believed that the novel composition of the present disclosure comprising an alkoxysilane, a non-hydroxide base, and protein denaturant, when used in combination with heat and an apparatus capable of physically smoothing the hair resulted in a highly efficacious system of straightening the hair or reducing the curl of hair as a result of an induced supercontraction and denaturation of hair protein.

Furthermore, it has been surprisingly found that by employing the process of the present invention, straightening/relaxing or curl reduction of hair can be achieved in a manner which is less harmful to a user's skin and hair than conventional hair straightening/relaxing or curl reducing processes.

Moreover, the subject composition and process and other compositions that may additionally be used in the subject process avoid use of formalin or formalin derivatives or formaldehyde-generating compounds that are employed in some conventional hair straightening/relaxing products and which are known to breakdown to formaldehyde with high heat, thereby generating dangerous fumes. Thus, the compositions and processes of the present disclosure are preferably substantially free of formalin, formalin derivative, formaldehyde, formaldehyde derivatives or formaldehyde donors and materials that may form or release formaldehyde when present in the composition, including preservatives that may form or release formaldehyde in the composition. The term "substantially free" as used herein means that the total amount of formaldehyde-generating compounds in the compositions of the present disclosure is less than about 0.1%, preferably less than about 0.05%, more preferably less than about 0.01%, and most preferably is 0%.

It is to be understood that the foregoing describes various exemplary embodiments of the invention, but that modifications may be made therein without departing from the spirit or scope of the invention as set forth in the claims.

The compositions and process of the present invention can comprise, consist of, or consist essentially of the essential elements and limitations of the invention described herein, as well as any additional or optional ingredients, components, or limitations described herein or otherwise useful in the field.

Non-Hydroxide Base

Suitable non-hydroxide bases for use in the present invention are those bases having a pKa of from about 0 to about 15, preferably from about 1 to about 14, and more preferably from about 2 to about 13. These may be chosen from organic bases and inorganic bases.

Organic bases generally include nitrogen-containing bases which do not completely disassociate in water. Examples thereof include, but are not limited to, alkylamines, alkyleneamines, alkanolamines, quinoline, aniline, pyridine, basic amino acids, and their derivatives. Particularly preferred nitrogen-containing bases include ethylenediamines, monoethanolamines, arginine, lysine, and their derivatives, and mixtures thereof. Most preferably, the non-hydroxide base is monoethanolamine (MEA).

Inorganic bases generally include alkali metal phosphates and carbonates such as, for example, sodium phosphate, potassium phosphate, sodium carbonate, sodium bicarbonate, potassium carbonate, potassium bicarbonate, and their derivatives.

Inorganic bases may also include alkali metals of carboxylates such as, for example, sodium acetate, potassium acetate, sodium citrate, and potassium citrate, and their derivatives. Particularly preferred inorganic bases include potassium phosphate, sodium phosphate, and sodium carbonate.

The non-hydroxide base is typically employed in the composition for reducing curl and/or frizziness of hair in an amount of from about 0.1% to about 50% by weight, preferably from about 0.2% to about 30% by weight, more preferably from about 0.5% to about 10% by weight, even more preferably from about 1% to about 5% by weight, such as about 1%, or such as about 2%, based on the total weight of the composition for reducing curl and/or frizziness of hair.

Protein Denaturant

Suitable protein denaturants for use in the present invention can be chosen from ureas, guanidines, amidines, urethanes, aromatic monohydroxylated, dihydroxylated, trihydroxylated or polyhydroxylated derivatives, nitrogen heterocycles of the imidazole or triazole family, carboxylic acids and amide and thioamide derivatives thereof, thioureas, amino acids, alcohols, polyols, amine oxides, surfactants containing sugar, choline, deoxycholine or polyethylene glycol units, metal salts and sulfamides.

As "urea" that may be used as relaxing active agent, this term refers to any derivative comprising in its chemical formula a carbonyl group simply bonded to 2 nitrogen atoms. These ureas are more particularly selected from the compounds of general formulae (I) and (II) below:

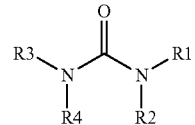

(I)

in which:

R1, R2, R3 and R4 represent, independently:

(i) a hydrogen atom, or (ii) a linear or branched lower C1-C4 alkyl or alkenyl radical, optionally substituted with a radical chosen from: hydroxyl, amino, dimethylamino, carboxyl or carboxamide or N-methylcarboxamide.

When R1, R2 and R3 represent a hydrogen atom, R4 may also denote a radical chosen from the following: carboxamide; methoxy; ethoxy; 1,2,4-triazolyl; cyclopentyl; methoxycarbonyl; ethoxycarbonyl; CO—CH═CH—COOH; phenyl optionally substituted with a chlorine atom or a hydroxyl radical; benzyl; or 2,5-dioxo-4-imidazolidinyl.

When R1 and R3 represent a hydrogen atom, R2 may also represent a hydrogen atom or a methyl or ethyl radical and R4 an acetyl radical.

When R1=R2=H, R3 and R4 may also form, with the nitrogen atom that bears them, a piperidine or 3-methylpyrazole or 3,5-dimethylpyrazole or maleimide ring.

Finally, R1 and R2, and also R3 and R4, may also form, with the nitrogen atom that bears them, an imidazole ring.

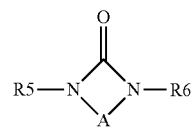

(II)

in which:

R5 and R6 represent, independently of each other:

(i) a hydrogen atom, or (ii) a linear or branched C1-C4 lower alkyl radical, optionally substituted with a radical chosen from: hydroxyl, amino, dimethylamino, carboxyl or carboxamide.

and A represents the radicals: CH2-CH2 or CH═CH or CH2-CO or CO—NH or CH═N or CO—CO or CHOH—CHOH or (HOOC)CH—CH or CHOH—CO or CH2-CH2-CH2 or CH2-NH—CO or CH═C(CH3)-CO or NH—CO—NH or CH2-CH2-CO or CH2-N(CH3)-CH2 or NH—CH2-NH or CO—CH(CH3)-CH2 or CO—CH2-CO or CO—NH—CO or CO—CH(COOH)—CH2 or CO—CH═C(COOH) or CO—CH═C(CH3) or CO—C(NH2)═CH or CO—C(CH3)═N or CO—CH═CH or CO—CH═N or CO—N═CH.

As "guanidine" that may be used as relaxing active agent, this term means any derivative comprising in its chemical formula at least one carbon atom doubly bonded to a nitrogen atom and singly bonded to two other nitrogen atoms. These guanidines are more particularly selected from the compounds of general formula (III) below:

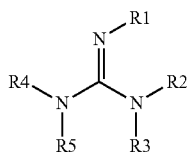

(III)

in which:

R1, R2, R3, R4 and R5 represent, independently:

(iii) a hydrogen atom, or (iv) a linear or branched C1-C4 lower alkyl or alkenyl radical, optionally substituted with one or two radicals chosen from: hydroxyl, amino, dimethylamino, methoxy, ethoxy, carboxyl, carboxamide, N-methylcarboxamide or SO 3H When R1, R2, R3 and R4 represent a hydrogen atom, R5 may also denote a radical chosen from the following: acetyl; chloroacetyl; carboxamide; methoxy; ethoxy; 1,2,4-triazolyl; cyclopentyl; methoxycarbonyl; ethoxycarbonyl; CO—CH=CH—COOH; phenyl optionally substituted with a chlorine atom or a hydroxyl radical; benzyl; thiazolidone; benzimidazole; benzoxazole; benzothiazole; or C(=NH)—NR6R7 in which R6 and R7 denote, independently of each other, a hydrogen atom or a linear or branched C1-C4 lower alkyl radical, optionally substituted with one or two radicals chosen from: hydroxyl, amino, dimethylamino, carboxyl and carboxamide; or N-methylcarboxamide; or alternatively a phenyl radical.

When R1=R2=R3=H, R4 and R5 may also form, with the nitrogen atom that bears them, a pyrrolidine, piperidine, pyrazole or 1,2,4-triazole ring, optionally substituted with one or two radicals chosen from: hydroxyl, amino and carboxyl.

When R1=R2=H, and R4=H or methyl, R3 and R5 may also together form a 5-membered ring optionally containing an oxo group, and the organic or mineral salts thereof.

The protein denaturant is preferably chosen from a urea or a guanidine, urea derivatives and/or salts, guanidine derivatives and/or salts, arginine, other compounds and their salts containing a guanidine moiety, and mixtures thereof.

In particular embodiments of the present disclosure, the hair treatment composition comprises at least two protein denaturants. The at least two protein denaturants are preferably chosen from a urea or a guanidine, urea derivatives and/or salts, guanidine derivatives and/or salts, arginine, other compounds and their salts containing a guanidine moiety, and mixtures thereof. Preferably, the at least two protein denaturants may be chosen from urea and hydroxyethyl urea.

Preferably, the at least two protein denaturants are used in combination, present in a ratio by weight ranging from about 10:1 to about 1:10, or such as from about 8:1 to about 1:8, or such as from about 5:1 to about 2:1. In certain embodiments, the at least two protein denaturants are used in combination, present in a ratio by weight of such as from about 5:1, or such as from about 3:1, or such as from about 1:1, or preferably, from about 2:1.

Preferably, at least one of the protein denaturants is an organic amine having a pKb greater than 12; and more preferably, having a pKb greater than 13 at 25° C., such as for example, urea.

Some of the protein denaturants may also fit the description of the non-hydroxide base and therefore, can be used as the non-hydroxide base according to the invention. In such a case, the protein denaturant(s) in the hair treatment composition are different from the non-hydroxide base.

The protein denaturant is typically employed in an amount of from about 0.1% to about 50% by weight, preferably from about 0.5% to about 40% by weight, preferably from about 1% to about 30% by weight, preferably from about 2% to about 20% by weight, based on the total weight of the composition for reducing curl and/or frizziness of hairreducing curl and/or frizziness of hairreducing curl and/or frizziness of hair.

Alkoxysilanes Comprising at Least One Solubilizing Functional Group

As used herein, the term "at least one solubilizing functional group" means any functional chemical group facilitating the bringing into solution of the alkoxysilane in the solvent or in a combination of solvents of the composition, for example, in solvents chosen from water, water-alcoholic mixtures, organic solvents, polar solvents and non-polar solvents.

Suitable solubilizing functional groups for use in accordance with the present disclosure include, but are not limited to, primary, secondary, and tertiary amine, aromatic amine, alcohol, carboxylic acid, sulfonic acid, anhydride, carbamate, urea, guanidine, aldehyde, ester, amide, epoxy, pyrrole, dihydroimidazole, gluconamide, pyridyle, and polyether groups.

The at least one alkoxysilane present in the composition comprises at least one solubilizing functional group, which may be identical or different, such as those previously defined.

The at least one alkoxysilane comprising at least one solubilizing functional group present in the composition of the present disclosure may comprise at least one silicon atom, for example, one silicon atom.

The at least one alkoxysilane comprising at least one solubilizing functional group present in the composition may, in at least one embodiment, comprise two or three alkoxy functions. In another embodiment, the alkoxy functional groups are chosen from methoxy and ethoxy functional groups.

According to a further embodiment, the at least one alkoxysilane comprising at least one solubilizing functional group present in the composition of the present disclosure is chosen from compounds of formula (I):

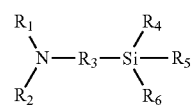

(I)

wherein:

$R_4$ is chosen from halogen atoms, OR' groups, and $R_{11}$ groups;

$R_5$ is chosen from halogen atoms, OR'' groups, and $R_{12}$ groups;

$R_6$ is chosen from halogen atoms, OR''' groups, and $R_{13}$ groups;

$R_1$, $R_2$, $R_3$, R', R'', R''', $R_{11}$, $R_{12}$, and $R_{13}$, which may be identical or different, are chosen from linear and branched, saturated and unsaturated hydrocarbon groups, optionally bearing at least one additional chemical group, wherein $R_1$, $R_2$, R', R'', and R''' may also be chosen from hydrogen; at least two groups $R_4$, $R_5$, and $R_6$ are different from $R_{11}$, $R_{12}$, and $R_{13}$, and at least two groups R', R'', and R''' are not hydrogen.

According to a second embodiment of the present disclosure, the at least one alkoxysilane comprising at least one solubilizing functional group present in the composition is chosen from compounds of formula (II):

(II)

wherein:

$R_9$ is chosen from halogen atoms and $OR'_9$ groups and $R_{10}$ is chosen from halogen atoms and $OR'_{10}$ groups; wherein at least one of $R_9$ and $R_{10}$ is not a halogen;

$R'_9$ and $R'_{10}$, which may be identical or different, are chosen from hydrogen, and linear and branched, saturated and unsaturated $C_1$-$C_{14}$ hydrocarbon groups; wherein at least one of $R_9$ and $R_{10}$ is not hydrogen;

$R_7$ is a non hydrolyzable functional group providing a cosmetic effect, and $R_8$ is a non hydrolyzable functional group bearing at least one function chosen from: amines, carboxylic acids and salts thereof, sulfonic acids and salts thereof, polyols such as glycol, polyethers such as polyalkylene ether, and phosphoric acids and salts thereof.

As used herein, the term "functional group providing a cosmetic effect" means a group derived from an entity chosen from reducing agents, oxidizing agents, coloring agents, polymers, surfactants, antibacterial agents, and UV absorbing filters.

According to a third embodiment of the present disclosure, the at least one alkoxysilane comprising at least one solubilizing functional group present in the composition of the present disclosure is chosen from compounds of formula (III):

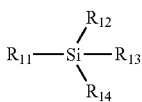

(III)

wherein:

$R_{12}$ is chosen from halogen atoms, $OR'_{12}$ groups, and $R_o$ groups;

$R_{13}$ is chosen from halogen atoms, $OR'_{13}$ groups, and $R'_o$ groups;

$R_{14}$ is chosen from halogen atoms, $OR'_{14}$ groups, and $R''_o$ groups;

wherein at least two groups $R_{12}$, $R_{13}$ and $R_{14}$ are different from $R_o$, $R'_o$, and $R''_o$ groups;

$R_{11}$ is a group chosen from groups bearing at least one function chosen from: carboxylic acids and salts thereof, sulfonic acids and salts thereof, and polyalkylethers; and Ro, R' o, R"o, $R'_{12}$, $R'_{13}$, and $R'_{14}$, which may be identical or different, are chosen from linear and branched, saturated and unsaturated, $C_1$-$C_{14}$ hydrocarbon groups optionally bearing at least one additional chemical functional group chosen from: carboxylic acids and salts thereof, sulfonic acids and salts thereof, and polyalkylether functions, wherein $R'_{12}$, $R'_{13}$, and $R_{14}$ may also be chosen from hydrogen, and wherein at least two of the groups $R'_{12}$, $R'_{13}$, and $R'_{14}$ are not hydrogen.

According to another embodiment of the present disclosure, the at least one alkoxysilane comprising at least one solubilizing functional group present in the composition of the present disclosure is chosen from compounds of formula (IV):

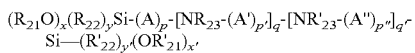

(IV)

wherein:

$R_{21}$, $R_{22}$, $R'_{21}$, and $R'_{22}$, which may be identical or different, are chosen from linear and branched, saturated and unsaturated hydrocarbon chains, optionally comprising at least one heteroatom, optionally interrupted by or substituted with at least one group chosen from ether, ester, amine, amide, carboxyl, hydroxyl, and carbonyl groups, x is an integer ranging from 1 to 3,
y=3-x,
x' is an integer ranging from 1 to 3,
y'=3-x',
p=0 or 1,
p'=0 or 1,
p"=0 or 1,
q=0 or 1,
q'=0 or 1,
wherein at least one of q or q' is not equal to zero, A, A', and A", which may be identical or different, are chosen from linear and branched $C_1$-$C_{20}$ alkylene divalent radicals, and $R_{23}$ and $R'_{23}$, which may be identical or different, are chosen from hydrogen and linear and branched, saturated and unsaturated hydrocarbon chains, optionally comprising at least one heteroatom, optionally interrupted by or substituted with at least one entity chosen from: ether, $C_1$-$C_{20}$ alcohol ester, amine, carboxyl, alkoxysilane, $C_6$-$C_{30}$ aryl, hydroxyl, and carbonyl groups, and aromatic, heterocyclic, and non-heterocyclic rings, optionally substituted with at least one group chosen from $C_3$-$C_{20}$ alcohol ester, amine, amide, carboxyl, alkoxysilane, hydroxyl, carbonyl, and acyl groups.

According to this embodiment, the at least one alkoxysilane comprising at least one solubilizing functional group may be chosen from compounds of formula (V):

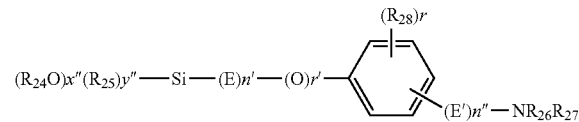

(V)

wherein:

$R_{24}$ and $R_{25}$, which may be identical or different, are chosen from linear and branched, saturated and unsaturated hydrocarbon chains, optionally comprising at least one heteroatom, optionally interrupted by or substituted with at least one group chosen from ether, ester, amine, amide, carboxyl, hydroxyl, and carbonyl groups, x"=2 or 3,
y"=3-x",
n"=0 or 1,
n"=0 or 1, E and E', which may be identical or different, are chosen from linear and branched $C_1$-$C_{20}$ alkylene divalent radicals, $R_{26}$ and $R_{27}$, which may be identical or different, are chosen from hydrogen and linear and branched, saturated and unsaturated hydrocarbon chains, optionally comprising at least one heteroatom, optionally interrupted by or substituted with at least one entity chosen from: ether, $C_1$-$C_{20}$ alcohol ester, amine, carboxyl, alkoxysilane, $C_6$-$C_{30}$ aryl, hydroxyl, and carbonyl groups, and aromatic, heterocyclic, and non-heterocyclic rings, optionally substituted with at least one group chosen from: $C_1$-$C_{20}$ alcohol ester, amine, amide, carboxyl, alkoxysilane, hydroxyl, carbonyl, and acyl groups, r is an integer ranging from 0 to 4,
r'=0 or 1, and
$R_{28}$, which may be identical or different, is chosen from hydrogen and linear and branched, saturated and unsaturated hydrocarbon chains, comprising, optionally at least one heteroatom, optionally interrupted by or substituted with at least one entity chosen from: ether, alkyl alcohol ester, amine, carboxyl, alkoxysilane, alkyl aryl, hydroxyl, and carbonyl groups, and aromatic, heterocyclic, and non-heterocyclic rings.

According to a further embodiment of the present disclosure, the at least one alkoxysilane comprising at least one solubilizing functional group present in the composition is chosen from compounds of formula (VI):

$$(R_{29}O)x_1(R_{30})y_1\text{-Si-}(A_1)_s\text{—CH}=\text{O} \qquad (VI)$$

wherein:
$R_{29}$ and $R_{30}$, which may be identical or different, are chosen from linear and branched, saturated and unsaturated hydrocarbon chains, optionally comprising at least one heteroatom, optionally interrupted by or substituted with at least one group chosen from ether, ester, amine, amide, carboxyl, hydroxyl, and carbonyl groups, $x_1=2$ or 3,
$y_1=3-x_1$,
$A_1$ is chosen from linear and branched $C_1$-$C_{20}$ alkylene divalent radicals, optionally interrupted by or substituted with at least one group chosen from $C_1$-$C_{30}$ alcohol ester, amine, carboxyl, alkoxysilane, $C_6$-$C_{30}$ aryl, hydroxyl, and carbonyl groups, and
s=0 or 1.

In a further embodiment, the at least one alkoxysilane comprising at least one solubilizing functional group is chosen from compounds of formula (VII):

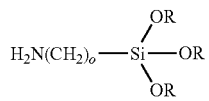

(VII)

wherein the R radicals, which may be identical or different, are chosen from $C_1$-$C_6$ alkyl radicals and n is an integer ranging from 1 to 6, for example, from 2 to 4.

The alkoxysilanes useful in the present disclosure can be chosen from alkoxysilanes comprising a silicon atom of formula $R_{(4-n)}SiX_n$, wherein X is a hydrolysable group such as methoxy, ethoxy or 2-methoxyethoxy, R is a monovalent organic radical which contains 1 to 12 carbon atoms and may contain groups such as mercapto, epoxy, acrylyl, methacrylyl, amino or urea, and n is an integer from 1 to 4, and according to at least one embodiment is 3. Possible examples of useful alkoxysilanes include 3-mercaptopropyltriethoxysilane and aminoalkyltrialkoxysilanes such as 3-aminopropyltriethoxysilane, as described in French Patent Application No. FR 2 789 896.

Other useful alkoxysilanes are cited, for example, in Patent Application EP 1 216 022, which describes alkoxysilanes comprising at least one hydrocarbon chain containing a non-basic solubilizing chemical function. In this respect, non-limiting mention may be made of the HCl-neutralized sodium N-[(3-trimethoxysilyl)propyl]ethylenediaminetriacetate supplied by GELEST.

According to at least one embodiment, the alkoxysilanes may comprise at least one hydrocarbon chain containing fluorine atoms. Possible examples include but are not limited to the 3,3,3-trifluoropropyltriethoxysilane or tridecafluorooctyltriethoxysilane compounds described in Patent Application EP 1 510 197.

In another embodiment, the useful alkoxysilanes may be alkoxysilanes which carry a group having a cosmetic functional group, such as aromatic nitro dyes or anthraquinone, napthoquinone, benzoquinone, azo, xanthene, triarylmethane, azine, indoaniline, indophenolic or indoamine dyes; groups having a reductive effect, such as thiol groups, sulphinic acid or sulphinic salt, it being possible for these alkoxysilanes to carry a solubilizing non-hydrolysable group such as amino groups, carboxylic acids, sulphonic acids, sulphates, quaternary ammoniums, polyalcohols, polyether and phosphates. One possible example includes aminopropyl-N-(4,2-dinitrophenyl)aminopropyldiethoxysilane. Compounds of this kind are described, for example, in Patent Application EP 1 216 023.

The alkoxysilanes of the present disclosure may be amino aryl alkoxysilanes. Possible examples include but are not limited to the following compounds:
3-(m-aminophenoxy)propyltrimethoxysilane, of the formula:

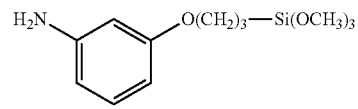

provided by GELEST,
p-aminophenyltrimethoxysilane, of formula:

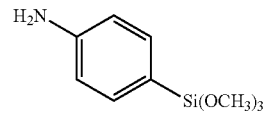

provided by GELEST, and
N-(2-aminoethylaminomethyl)phenethyltrimethoxysilane, of the formula:

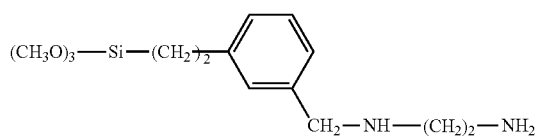

provided by GELEST.

The alkoxysilanes of the present disclosure may also be silanes having an aldehyde or acetal functional group.

The alkoxysilanes may also be silanes containing non-primary amines, such as the bis[3-(triethoxysilyl)propyl] amine of the formula $(CH_3CH_2O)_3$—$Si(CH_2)_3NH(CH_2)_3Si(OCH_2CH_3)_3$ provided by Fluorochem, the bis[trimethoxysilylpropyl]amine of the formula $(CH_3O)_3$—$Si(CH_2)_3NH(CH_2)_3Si(OCH_3)_3$ provided by Gelest, the bis[methyldiethoxysilylpropyl]amine of the formula $(CH_3CH_2O)_2CH_3Si(CH_2)_3NH(CH_2)_3SiCH_3$ $(OCH_2CH_3)_2$ provided by Gelest and the bis[3-trimethoxysilylpropyl]ethylenediamine of formula $(CH_3O)_3Si(CH_2)_3NH(CH)_2NH$ $(CH_2)_3Si(OCH_3)_3$ provided by Gelest.

In another embodiment the at least one alkoxysilane is a trialkoxysilane comprising an amino substituent.

In a particularly preferred embodiment, the at least one alkoxysilane comprising at least one solubilizing functional group present in the composition of the present disclosure is γ-aminopropyltriethoxysilane, also known as 3-aminopropyltriethoxysilane, commercially available under the tradename, KBE-903™, from Shin-Etsu, and also under the tradename, Silsoft® A-1100, from Momentive Performance Materials.

The at least one alkoxysilane comprising at least one solubilizing functional group may be present in the composition from about 0.1% to about 20% by weight, preferably from about 0.05% to about 30% by weight preferably from about 0.5% to about 15% by weight, preferably from about 1% to about 10% by weight, such as from about 1% to about 5% by weight, or such as from about 5% to about 10% by weight, based on the total weight of the composition for reducing curl and/or frizziness of hair.

Fatty Substance

The composition for reducing curl and/or frizziness of hair of the present invention may further comprise at least one fatty substance.

"Fatty substance" means an organic compound insoluble in water at normal temperature (25) and at atmospheric pressure (760 mmHg) (solubility below 5% and such as below 1% and further such as below 0.1%). Fatty substances have in their structure a chain of at least two siloxane groups or at least one hydrocarbon chain having at least 6 carbon atoms. Moreover, fatty substances are generally soluble in organic solvents in the same conditions of temperature and pressure, for example in chloroform, ethanol, benzene or decamethylcyclopentasiloxane.

Fatty substances are, for example, chosen from lower alkanes, fatty alcohols, esters of fatty acid, esters of fatty alcohol, oils such as mineral, vegetable, animal and synthetic non-silicone oils, non-silicone waxes and silicones and fatty acids.

In some embodiments, the alcohols and esters have at least one linear or branched, saturated or unsaturated hydrocarbon group, comprising 6 to 30 carbon atoms, optionally substituted, for example, with at least one hydroxyl group (for example 1 to 4). If they are unsaturated, these compounds can have one to three, conjugated or unconjugated, carbon-carbon double bonds.

With regard to the lower alkanes, in some embodiments, these have from 6 to 16 carbon atoms and are linear or branched, optionally cyclic. As examples, alkanes can be chosen from hexane and dodecane, isoparaffins such as isohexadecane and isodecane.

Non-limiting examples of non-silicone oils usable in the composition of the disclosure, include: hydrocarbon oils of animal origin, such as perhydrosqualene; hydrocarbon oils of vegetable origin, such as liquid triglycerides of fatty acids having from 6 to 30 carbon atoms such as triglycerides of heptanoic or octanoic acids, or for example sunflower oil, maize oil, soya oil, cucurbit oil, grapeseed oil, sesame oil, hazelnut oil, apricot oil, macadamia oil, arara oil, sunflower oil, castor oil, avocado oil, triglycerides of caprylic/capric acids such as those sold by the company Stearineries Dubois or those sold under the names MIGLYOL® 810, 812 and 818 by the company Dynamit Nobel, jojoba oil, shea butter oil; hydrocarbons with more than 16 carbon atoms, linear or branched, of mineral or synthetic origin, such as paraffin oils, petroleum jelly, liquid paraffin, polydecenes, hydrogenated polyisobutene such as Parleam®. fluorinated, partially hydrocarbon oils; as fluorinated oils, non-limiting examples include perfluoromethylcyclopentane and perfluoro-1,3-dimethylcyclohexane, sold under the names "FLUTEC® PC1" and "FLUTEC® PC3" by the company BNFL Fluorochemicals; perfluoro-1,2-dimethylcyclobutane; perfluoroalkanes such as dodecafluoropentane and tetradecafluorohexane, sold under the names "PF 5050®" and "PF 5060®" by the 3M Company, or bromoperfluorooctyl sold under the name "FORALKYL®" by the company Atochem; nonafluoro-methoxybutane and nonafluoroethoxyisobutane; derivatives of perfluoromorpholine, such as 4-trifluoromethyl perfluoromorpholine sold under the name "PF 5052®" by the 3M Company.

The fatty alcohols usable as fatty substances in the composition of the disclosure include, but are not limited to, non-alkoxylated, saturated or unsaturated, linear or branched, and have from 6 to 30 carbon atoms and more particularly from to 30 carbon atoms; For example, cetyl alcohol, stearyl alcohol and their mixture (cetylstearyl alcohol), octyldodecanol, 2-butyloctanol, 2-hexyldecanol, 2-undecylpentadecanol, oleic alcohol or linoleic alcohol.

The exemplary non-silicone wax or waxes that can be used in the composition of the disclosure are chosen from carnauba wax, candelilla wax, and Alfa wax, paraffin wax, ozokerite, vegetable waxes such as olive wax, rice wax, hydrogenated jojoba wax or absolute waxes of flowers such as the essential wax of blackcurrant flower sold by the company BERTIN (France), animal waxes such as beeswaxes, or modified beeswaxes (cerabellina); other waxes or waxy raw materials usable according to the disclosure are, for example, marine waxes such as that sold by the company SOPHIM under reference M82, waxes of polyethylene or of polyolefins in general.

The exemplary fatty acid esters are the esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total number of carbons of the esters being, for example, greater than or equal to 10.

Among the monoesters, non-limiting mentions can be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methyl acetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, ethyl-2-hexyl palmitate, 2-octyldecyl palmitate, alkyl myristates such as isopropyl, butyl, cetyl, 2-octyldodecyl, myristyl, stearyl myristate, hexyl stearate, butyl stearate, isobutyl stearate; dioctyl malate, hexyl laurate, and 2-hexyldecyl laurate.

Further non-limiting mentions of esters can be made of the esters of $C_4$-$C_{22}$ di- or tricarboxylic acids and of $C_1$-$C_{22}$ alcohols and the esters of mono-, di- or tricarboxylic acids and of $C_2$-$C_{26}$ di-, tri-, tetra- or pentahydroxy alcohols.

Even further non-limiting examples of esters include: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate, tridecyl erucate; triisopropyl citrate; triisostearyl citrate; glyceryl trilactate; glyceryl trioctanoate; trioctyldodecyl citrate; trioleyl citrate, propylene glycol dioctanoate; neopentyl glycol diheptanoate; diethylene glycol diisanonate; and polyethylene glycol distearates.

Among the esters mentioned above, exemplary esters include ethyl, isopropyl, myristyl, cetyl, stearyl palmitates, ethyl-2-hexyl palmitate, 2-octyldecyl palmitate, alkyl myristates such as isopropyl, butyl, cetyl, 2-octyldodecyl myristate, hexyl stearate, butyl stearate, isobutyl stearate; dioctyl malate, hexyl laurate, 2-hexyldecyl laurate and isononyl isononanate, cetyl octanoate.

The composition can also comprise, as fatty ester, esters and di-esters of sugars of $C_6$-$C_{30}$, such as $C_{12}$-$C_{22}$ fatty acids. "Sugar" as used in the disclosure means oxygen-containing hydrocarbon compounds that possess several alcohol functions, with or without aldehyde or ketone functions, and having at least 4 carbon atoms. These sugars can be monosaccharides, oligosaccharides or polysaccharides.

As suitable sugars, non-limiting examples include sucrose, glucose, galactose, ribose, fucose, maltose, fructose, mannose, arabinose, xylose, lactose, and their derivatives, for example alkylated, such as methylated derivatives such as methylglucose.

The esters of sugars and of fatty acids can, for example, be chosen from the esters or mixtures of esters of sugars described previously and of linear or branched, saturated or unsaturated $C_6$-$C_{30}$, such as $C_{12}$-$C_{22}$ fatty acids. If they are unsaturated, these compounds can have one to three, conjugated or unconjugated, carbon-carbon double bonds.

The esters according to at least one embodiment can also be chosen from mono-, di-, tri- and tetra-esters, polyesters and mixtures thereof.

These esters can be for example oleate, laurate, palmitate, myristate, behenate, cocoate, stearate, linoleate, linolenate, caprate, arachidonates, or mixtures thereof such as the oleopalmitate, oleo-stearate, palmito-stearate mixed esters.

For example, the mono- and di-esters can be used, and such as the mono- or di-oleate, stearate, behenate, oleopalmitate, linoleate, linolenate, oleostearate, of sucrose, of glucose or of methylglucose.

Non-limiting mention can be made of the product sold under the name GLUCATE® DO by the company Amerchol, which is a dioleate of methylglucose.

Exemplary esters or of mixtures of esters of sugar of fatty acid include: the products sold under the names F160, F140, F110, F90, F70, SL40 by the company Crodesta, denoting respectively the palmito-stearates of sucrose formed from 73% of monoester and 27% of di- and tri-ester, from 61% of monoester and 39% of di-, tri-, and tetra-ester, from 52% of monoester and 48% of di-, tri-, and tetra-ester, from 45% of monoester and 55% of di-, tri-, and tetra-ester, from 39% of monoester and 61% of di-, tri-, and tetra-ester, and the monolaurate of sucrose; the products sold under the name Ryoto Sugar Esters for example with the reference B370 and corresponding to the behenate of sucrose formed from 20% of monoester and 80% of di-triester-polyester; sucrose mono-di-palmito-stearate marketed by the company Goldschmidt under the name TEGOSOFT® PSE.

The silicones usable in the composition of the present disclosure include but are not limited to volatile or non-volatile, cyclic, linear or branched silicones, modified or not with organic groups, having a viscosity from $5\times10^{-6}$ to 2.5 $m^2$/s at 25, such as from $1\times10^{-5}$ to 1 $m^2$/s.

The silicones usable according to the disclosure can be in the form of oils, waxes, resins or gums.

In some embodiments, the silicone is chosen from the polydialkylsiloxanes, such as the polydimethylsiloxanes (PDMS), and the organo-modified polysiloxanes having at least one functional group selected from the poly(alkoxylated) groups, the amine groups and the alkoxy groups.

The organopolysiloxanes are defined in more detail in the work of Walter NOLL "Chemistry and Technology of Silicones" (1968), Academic Press. They can be volatile or non-volatile.

When they are volatile, the silicones are, for example, chosen from those with a boiling point between 60. and 260, and for further examples, chosen from:

the cyclic polydialkylsiloxanes having from 3 to 7, such as from 4 to 5 silicon atoms. It can be, for example, the octamethylcyclotetrasiloxane marketed under the name VOLATILE SILICONE® 7207 by UNION CARBIDE or SILBIONE® 70045 V2 by RHODIA, the decamethylcyclopentasiloxane marketed under the name VOLATILE SILICONE® 7158 by UNION CARBIDE, and SILBIONE® 70045 V5 by RHODIA, and mixtures thereof.

Non-limiting mentions can also be made of the cyclocopolymers of the dimethylsiloxanes/methylalkylsiloxane type, such as SILICONE VOLATILE® FZ 3109 marketed by the company UNION CARBIDE, of the formula V:

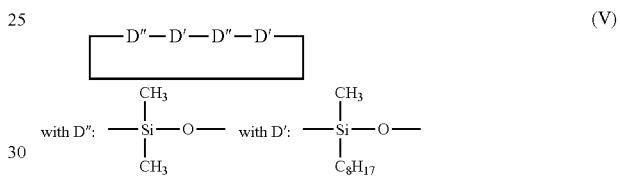

Non-limiting mentions can further be made of the mixtures of cyclic polydialkylsiloxanes with organic compounds derived from silicon, such as the mixture of octamethylcyclotetrasiloxane and tetratrimethylsilylpentaerythritol (50/50) and the mixture of octamethylcyclotetrasiloxane and oxy-1,1'-(hexa-2,2,2',2',3,3'-trimethylsilyloxy)bis-neopentane.

Other suitable volatile silicones include the linear volatile polydialkylsiloxanes having 2 to 9 silicon atoms and with a viscosity less than or equal to $5\times10^{-6}$ $m^2$/s at 25. An example is decamethyltetrasiloxane, marketed under the name "SH 200" by the company TORAY SILICONE. Silicones included in this class are also described in the article published in Cosmetics and Toiletries, Vol. 91, January 76, p. 27-32-TODD BYERS "Volatile Silicone fluids for cosmetics".

Even further non-limiting mentions can be made of non-volatile polydialkylsiloxanes, gums and resins of polydialkylsiloxanes, polyorganosiloxanes modified with the aforementioned organofunctional groups, and mixtures thereof.

These silicones are, for example, chosen from the polydialkylsiloxanes, such as the polydimethylsiloxanes with trimethylsilyl end groups. The viscosity of the silicones is measured at 25 according to standard ASTM 445 Appendix C.

Among these polydialkylsiloxanes, mention can be made of, non-exhaustively, the following commercial products: the SILBIONE® oils of series 47 and 70 047 or the MIRASIL® oils marketed by RHODIA, for example the oil 70 047 V 500 000; the oils of the MIRASIL® series marketed by the company RHODIA; the oils of the 200 series from the company DOW CORNING such as DC200, with a viscosity of 60 000 $mm^2$/s; the VISCASIL® oils from GENERAL ELECTRIC and certain oils of the SF series (SF 96, SF 18) from GENERAL ELECTRIC.

Non-limiting mention can also be made of the polydimethylsiloxanes with dimethylsilanol end groups known under the name of dimethiconol (CTFA), such as the oils of the 48 series from the company RHODIA.

In this class of polydialkylsiloxanes, non-limiting mentions can be made of the products marketed under the names "ABIL WAX® 9800 and 9801" by the company GOLDSCHMIDT, which are polydialkyl ($C_1$-$C_{20}$) siloxanes.

The silicone gums usable according to the disclosure are, for example, polydialkylsiloxanes, such as polydimethylsiloxanes with high number-average molecular weights between 200,000 and 1,000,000 used alone or mixed in a solvent. This solvent can be chosen from the volatile silicones, the polydimethylsiloxane (PDMS) oils, the polyphenylmethylsiloxane (PPMS) oils, the isoparaffins, the polyisobutylenes, methylene chloride, pentane, dodecane, tridecane and mixtures thereof.

Products usable according to the disclosure are, for example, mixtures such as: mixtures formed from a chain end hydroxylated polydimethylsiloxane, or dimethiconol (CTFA) and a cyclic polydimethylsiloxane also called cyclomethicone (CTFA), such as the product Q2 1401 marketed by the company DOW CORNING; mixtures of a polydimethylsiloxane gum and a cyclic silicone such as the product SF 1214 Silicone Fluid from the company GENERAL ELECTRIC, said product being a gum SF corresponding to a dimethicone, having a number-average molecular weight of 500,000, dissolved in the oil SF 1202 Silicone Fluid corresponding to decamethylcyclopentasiloxane; mixtures of two PDMS of different viscosities, for example, of a PDMS gum and a PDMS oil, such as the product SF 1236 from the company GENERAL ELECTRIC. The product SF 1236 is a mixture of a gum SE 30 as defined above having a viscosity of 20 $m^2$/s and an oil SF 96 with a viscosity of $5 \times 10^{-6}$ $m^2$/s. This product, for example, has 15% of gum SE 30 and 85% of oil SF 96.

The organopolysiloxane resins usable according to the disclosure include but are not limited to crosslinked siloxane systems containing the units: $R_2SiO_{2/2}$, $R_3SiO_{1/2}$, $RSiO_{3/2}$ and $SiO_{4/2}$ in which R represents an alkyl having 1 to 16 carbon atoms. For example, R denotes a $C_1$-$C_4$ lower alkyl group such as methyl.

Among these resins, non-limiting mention can be made of the product marketed under the name "DOW CORNING 593" or those marketed under the names "SILICONE FLUID SS 4230 and SS 4267" by the company GENERAL ELECTRIC, which are silicones of dimethyl/trimethyl siloxane structure.

Non-limiting mention can also be made of the resins of the trimethylsiloxysilicate type, such as those marketed under the names X22-4914, X21-5034 and X21-5037 by the company SHIN-ETSU.

The organomodified silicones usable according to the disclosure include but are not limited to silicones as defined previously, having in their structure at least one organofunctional group fixed by a hydrocarbon group.

In addition to the silicones described above, the organomodified silicones can be polydiaryl siloxanes, such as polydiphenylsiloxanes, and polyalkyl-arylsiloxanes functionalized by the aforementioned organofunctional groups.

The polyalkarylsiloxanes are, for example, chosen from the polydimethyl/methylphenylsiloxanes, the polydimethyl/diphenylsiloxanes, linear and/or branched, with viscosity ranging from $1 \times 10^{-5}$ to $5 \times 10^2$ $m^2$/s at 25.

Among these polyalkarylsiloxanes, non-limiting mentins can be made of the products marketed under the following names: the SILBIONE® oils of series 70 641 from RHODIA; the oils of the series RHODORSIL® 70 633 and 763 from RHODIA; the oil DOW CORNING 556 COSMETIC GRADE FLUID from DOW CORNING; the silicones of the PK series from BAYER such as the product PK20; the silicones of the series PN, PH from BAYER such as the products PN1000 and PH1000; certain oils of the SF series from GENERAL ELECTRIC such as SF 1023, SF 1154, SF 1250, SF 1265.

Among the organomodified silicones, non-limiting mention can be made of the polyorganosiloxanes having: polyoxyethylene and/or polyoxypropylene groups optionally with $C_6$-$C_{24}$ alkyl groups such as the products called dimethicone copolyol marketed by the company DOW CORNING under the name DC 1248 or the oils SILWET® L 722, L 7500, L 77, L 711 from the company UNION CARBIDE and the alkyl ($C_{12}$)-methicone copolyol marketed by the company DOW CORNING under the name Q2 5200; substituted or unsubstituted amine groups such as the products marketed under the name GP 4 Silicone Fluid and GP 7100 by the company GENESEE or the products marketed under the names Q2 8220 and DOW CORNING 929 or 939 by the company DOW CORNING. The substituted amine groups are, for example, $C_1$-$C_4$ aminoalkyl groups; alkoxylated groups, such as the product marketed under the name "SILICONE COPOLYMER F-755" by SWS SILICONES and ABIL WAX® 2428, 2434 and 2440 by the company GOLDSCHMIDT.

In some embodiments, the at least one fatty substance is neither alkoxylated, nor glycerolated.

For example, the at least one fatty substance is chosen from compounds that are liquid or pasty at room temperature and at atmospheric pressure.

For further example, the at least one fatty substance is a compound that is liquid at a temperature of 25 and at atmospheric pressure.

The at least one fatty substance is, for example, chosen from the lower alkanes, fatty alcohols, esters of fatty acid, esters of fatty alcohol, and oils such as non-silicone mineral, vegetable and synthetic oils, the silicones.

According to at least one embodiment, the at least one fatty substance is chosen from liquid paraffin, polydecenes, liquid esters of fatty acids and of fatty alcohols, and mixtures thereof, for example, the at least one fatty substance of the composition according to the disclosure can be non-silicone.

In some embodiments, the at least one fatty substance is chosen from alkanes, hydrocarbons and silicones.

The composition according to the disclosure comprises at least one fatty substance, which is preferably present in the composition in an amount of at least 10% by weight relative to the total weight of the composition. For example, the concentration of fatty substances is from about 10 to about 80% by weight, such as from about 15 to about 65% by weight, further such as from about 20 to about 55% by weight, based on the total weight of the composition for reducing curl and/or frizziness of hair.

Cosmetically Acceptable Carrier

As used herein, the term "cosmetically acceptable carrier" is known to one of ordinary skill in the art, and may comprise, for example, water and/or at least one organic solvent.

Cosmetically acceptable carriers useful according to various embodiments described herein may, by way of non-limiting example, be chosen from water, organic solvents, natural oils, synthetic oils, esters, hydrocarbons, silicones, and mixtures thereof. Non-limiting examples of cosmetically acceptable carriers include alcohols, such as ethanol, isopropyl alcohol, benzyl alcohol and phenyl ethyl alcohol; glycols and glycol ethers, such as propylene glycol, hexylene glycol, ethylene glycol monomethyl, monoethyl or monobutyl ether, propylene glycol and its ethers, such as propylene glycol monomethyl ether, butylene glycol, dipropylene glycol, and also diethylene glycol alkyl ethers, such as diethylene glycol monoethyl ether and monobutyl ether; hydrocarbons such as straight chain hydrocarbons, mineral oil, polybutene, hydrogenated polyisobutene, hydrogenated polydecene, polydecene, squalene, petrolatum and isoparaffins; and mixtures thereof, to name a few.

The composition for reducing curl and/or frizziness of hair according to the present disclosure may be, for example, in the form of a thickened cream so as to hold the hair as stiff as possible. These creams are made in the form of "heavy" emulsions, for example, based on glyceryl stearate, glycol stearate, self-emulsifying waxes, fatty alcohols, mineral oil and petrolatum.

Liquids or gels containing thickeners, such as carboxyvinyl polymers or copolymers that "stick" the hairs together and hold them in a smooth position during the leave-in time, may also be used.

Conditioning Agent

The conditioning agent that is optionally employed in the present invention may be chosen from plant oils, synthetic oils, silicones, esters, humectants, conditioning polymers, cationic agents and mixtures thereof. The conditioning agent may be applied directly onto hair by itself or may be delivered to the hair in a cosmetically acceptable carrier as described above.

Examples of plant oils are hydrocarbon-based plant oils with a high triglyceride content consisting of fatty acid esters of glycerol, the fatty acids of which may have varied chain lengths, these chains possibly being linear or branched, and saturated or unsaturated.

Other contemplated oils include synthetic oils or esters of formula $R_5COOR_6$ in which $R_5$ represents a linear or branched higher fatty acid residue, and $R_6$ represents a branched hydrocarbon-based chain.

Examples of other conditioning agents are branched and unbranched hydrocarbons and hydrocarbon waxes including polyolefins, in particular Vaseline (petrolatum), paraffin oil, squalane, squalene, hydrogenated polyisobutene, hydrogenated polydecene, polybutene, mineral oil, pentahydrosqualene, ceramides, and mixtures thereof.

Examples of silicones are silicone oils which include, but are not limited to, linear polydimethylsiloxanes (PDMSs), that are liquid at room temperature; polydimethylsiloxanes comprising alkyl, alkoxy or phenyl groups, which are pendent and/or at the end of a silicone chain, these groups each containing from 2 to 24 carbon atoms; phenylsilicones, for instance phenyl trimethicones, phenyl dimethicones, phenyl trimethylsiloxydiphenylsiloxanes, diphenyl dimethicones, diphenyl methyldiphenyl trisiloxanes, 2-phenylethyl trimethylsiloxysilicates, trimethyl pentaphenyl trisiloxane, tetramethyl hexaphenyl trisiloxane Examples of cationic agents which are suitable conditioning agent are behentrimonium chloride, cetrimonium chloride, quaternium-87, polyquaternium-6, polyquaternium-7, polyquaternium-10, and polyquaternium-37.

The conditioning agent may be delivered to the hair as a hair conditioner composition which may be in the form of a spray, liquid, cream, gel, lotion, mousse, foam, wax or paste.

The conditioning agent may be employed in the hair conditioner composition in an amount of from about 0.01 to about 40% by weight, such as from about 0.05 to about 30% by weight, further such as from about 0.1 to about 20% by weight, based on the weight of the hair conditioner composition.

Neutralizing Composition

The neutralizing composition that may be employed on the hair after the step of smoothing the treated hair using a combination of heat and means for physically smoothing hair may be provided in a cosmetically acceptable carrier as described above and may comprise other cosmetic ingredients.

In some embodiments, the neutralizing composition of the present invention includes at least one neutralizing ingredient including, but not limited to, at least one acid such as salicylic acid, citric acid and mixtures thereof, hydrogen peroxide and sodium bromate.

The pH of the neutralizing composition of the present invention is below about 7, more preferably, from about 2 to about 6, even more preferably from about 2 to about 5.

Auxiliary Ingredients

The composition for reducing curl and/or frizziness of hair, the conditioning agent and the neutralizing compositions as disclosed herein may also comprise at least one auxiliary ingredient chosen from, for example, dyeing agents, colorants, silicones in soluble, dispersed and microdispersed forms, nonionic, anionic, cationic and amphoteric surfactants, ceramides, glycoceramides and pseudoceramides, vitamins and provitamins including panthenol, waxes other than ceramides, glycoceramides and pseudoceramides, water-soluble and liposoluble, silicone-based and non-silicone-based sunscreens, nacreous agents and opacifiers, sequestering agents, plasticizers, solubilizers, acidifying agents, mineral and organic thickeners, antioxidants, hydroxy acids, penetrating agents, fragrances, and preserving agents.

In the event that surfactants are employed in the composition for reducing curl and/or frizziness of hair, said composition may be used as a shampoo. Similarly, in the event that one were to decide to use the composition of the invention as a hair conditioner, various types of conditioning agents can be added to the composition in order to facilitate this hair treating property.

According to one embodiment of the present disclosure, there is provided a process for reducing curl and/or frizziness of hair including first providing a composition for reducing curl and/or frizziness of hair, said composition containing, in a cosmetically acceptable carrier, at least one non-hydroxide base, at least one protein denaturant different from the non-hydroxide base, at least one alkoxysilane comprising at least one solubilizing functional group, and, optionally, at least one fatty substance, followed by contacting the hair with the composition for reducing curl and/or frizziness of hair to form treated hair, smoothing the hair using a combination of heat and means for physically smoothing hair to form smoothed hair, optionally, shampooing the smoothed hair, and rinsing the smoothed hair with water.

The optional step of shampooing the treated hair involves the application of a shampoo onto the treated hair wherein the shampoo comprises at least one anionic surfactant in a cosmetically acceptable carrier.

In certain embodiments of the present invention, the composition for reducing curl and/or frizziness of hair comprises, in a cosmetically acceptable carrier, at least one non-hydroxide base; at least one protein denaturant different from the at least one non-hydroxide base; at least one alkoxysilane comprising at least one solubilizing functional group; and at least one fatty substance.

The contact time (processing time) of the compositions for reducing curl and/or reducing frizziness with the hair is preferably, for less than about sixty minutes, and is more preferably, up to about twenty minutes.

In other embodiments, the contact time of the composition for reducing curl and/or reducing frizziness with the hair is up to about 10 minutes, particularly when the process of the present disclosure is used as a maintenance regimen, i.e., as a follow up procedure to maintain the curl pattern or further reduce the curl of the hair.

In certain embodiments, after the processing time has elapsed, the treated hair is contacted with at least one conditioning agent prior to the step of smoothing the hair using a combination of heat and means for physically smoothing hair.

The smoothing step of the present disclosure, using a combination of heat and means for physically smoothing hair to form smoothed hair, preferably includes the use of a flat iron or a blow dryer in combination with a comb, a brush, or an iron. The smoothing step of the present invention is preferably conducted at a temperature of at least 30° C.; preferably at least 50° C.; preferably at least 70° C. The heat in the smoothing step may emanate from any suitable source such as, for example, a hair dryer or blow dryer or hot/flat iron or an infrared heat generator/hair dryer in one device (e.g., Rollerball brand).

Typically, the lower the amount of non-hydroxide base present in the composition for reducing curl and/or frizziness of hair, the lower the temperature required at the smoothing step. Conversely, the amount of heat applied onto the treated hair can depend on the original hair type and/or the degree of damage to the hair.

The means for physically smoothing hair can be any apparatus capable of physically smoothing the hair such as, for example, a hair brush or comb. In one embodiment, the means for smoothing hair also serves as the source for generating heat such as, for example, a hot/flat iron.

The smoothed hair may also be contacted with a neutralizing composition having a pH of below about 7 to form neutralized hair, followed by rinsing the neutralized hair with water. The neutralizing composition may be in the form of a shampoo or a conditioner.

Optionally, the hair may also first be contacted with a pre-alkalizing composition having a pH of from about 8.0 to about 12.0 to form pre-alkalized hair prior to application of the curl/frizziness reducing composition. This pre-alkalizing step renders the process for reducing the curl and/or frizziness of hair more efficient and less time-consuming.

The pre-alkalizing step comprises contacting the hair with a pre-alkalizing composition which may be provided in any suitable form. Examples thereof include, but are not limited to, a shampoo, a conditioner or an alkaline solution in general. In a particularly preferred embodiment, the alkaline composition is in the form of a shampoo which would facilitate both the pre-alkalizing and cleaning of the hair at the same time.

Thus, in one embodiment of the present invention, there is provided a process for reducing curl and/or frizziness of hair that includes first pre-alkalizing or treating the hair with the alkaline composition before contacting the hair with the composition for reducing curl and/or frizziness of hair to form treated hair. Preferably, the alkaline composition is rinsed from the hair and the hair is dried, blown dry, prior to contacting the hair with the composition for reducing curl and/or frizziness of hair.

The pH of the pre-alkalizing composition can range from above 7 to about 12, such as from about 7.5 to 12, or such as from about 7.5 to about 10 or such as from about 8 to about 12 or such as from about 8 to about 10.

Due to the less caustic and the lower concentrations of the non-hydroxide compound being used, a barrier substance is not required when using the composition of the present invention for reducing curl and/or frizziness of hair. Commercially available hair relaxing products oftentimes require the hair stylist to apply a barrier substance such as petrolatum to the skin surrounding the scalp and the area around the ears. The barrier substance is used to prevent the skin from becoming irritated if the hair relaxing product contacts the skin. Thus, a barrier substance is not necessary when using the process of the present invention because the concentration and therefore, the degree of irritation of the non-hydroxide compound, are much lower.

EXAMPLES

Example I

Formulation Examples

| A. Compositions for reducing curl and/or frizziness of hair | | | |
|---|---|---|---|
| Ingredients | formula A % by weight | formula B % by weight | formula C % by weight |
| Monoethanolamine | 1.0 | 2.0 | 2.0 |
| 3-aminopropyltriethoxysilane (APTES) | 1.0 | 2.0 | 2.0 |
| Urea | 10.0 | 10.0 | 10 |
| Hydroxyethylurea | 5.0 | 5.0 | 5 |
| Hexylene Glycol | 2.0 | 2.0 | 2 |
| Amodimethicone* and trideceth-5 and trideceth-10 | 6.6 | 6.6 | — |
| Olive oil | — | — | 20 |
| Water | QS | QS | QS |

*15% activity in WACKER-BELSIL ® ADM LOG 1, commercially available from Wacker Chemie Ag.

| B. Conditioning Agent (Optional Treatment) | |
|---|---|
| Ingredients | % by weight |
| Behentrimonium chloride | 1.0 |
| Amodimethicone* and trideceth-5 and trideceth-10 | 5.3 |
| Quaternium-87 | 3.4 |
| Emulsifiers | 4.0 |
| Water | QS |

*15% activity in WACKER-BELSIL ® ADM LOG 1, commercially available from Wacker Chemie Ag.

| C. Neutralizing Composition (Optional treatment) | |
|---|---|
| Ingredients | % by weight |
| Nonionic surfactants: PPG-5-ceteth-10 phosphate, dimethicone PEG-7 phosphate, PPG-5-ceteth-20 | 3.5 |
| Sodium acrylate/sodium acryloyldimethyl taurate copolymer and isohexadecane and polysorbate 80 | 7.0 |
| Dimethicone | 1.0 |
| Citric acid | 0.0 |
| Sodium benzoate | 0.5 |
| Water | QS |

Example II

Straightening Efficiency (Efficiency of Reducing the Curl of Hair)

General procedure to test the straightening efficiency of the invention on Wavy Hair:

The tests were done on approximately 2.7 g hair swatches made of natural brown wavy hair, approximately 220-235 mm long (full length when straight). The following treatments were performed:

The hair swatches were shampooed with an alkaline shampoo two times. The shampooed hair swatches were blow dried to 100% dry. The dried swatches were then treated with the test compositions (see below) according to a processing time of 20 minutes. The treated hair swatches were then smoothened with simultaneous application of heat by passing a flat iron (400° F.) through the hair 3 times. The swatches were treated with the neutralizing composition which was allowed to remain on the hair for 5 minutes before shampooing and rinsing. The swatches were dried in ambient conditions then placed in controlled humidity (20% relative humidity (RH) overnight, then in 80% RH for 2 hours before taking measurements. The straightening efficiency (% SE) was calculated using the following formula:

$$\% \, SE = (Lf - Li)/(Ls - Li) \times 100$$

Where:
Lf=Final Length of the swatch (after air dry)
Li=Initial length of the swatch (before ironing)
Ls=Straight Length of the swatch (222 mm)

| Example | Test Compositions | % SE |
|---|---|---|
| 1 | Shampoo only | −38.8 |
| 2 | 2% monoethanolamine + 1.975% Hydroxyethyl Urea + 10% Urea + 2% hexylene glycol + water (Q.S.) | 36.4 |
| 3 | 2% monoethanolamine + 1.975% Hydroxyethyl Urea + 10% Urea + 2% Aminopropyl Triethoxysilane + 2% hexylene glycol + water (Q.S.) | 87.1 |
| 4 | 2% monoethanolamine + 1.975% Hydroxyethyl Urea + 10% Urea + 2% Aminopropyl Triethoxysilane + 20% Olive oil + 2% hexylene glycol + water (Q.S.) | 101.2 |

The results in the table above show that the hair straightening efficiency was significantly greater for Examples 2, 3, and 4, compared to example 1 (shampoo alone) and the straightening efficiency increased when the alkoxysilane and the fatty substance (olive oil) were present in the compositions.

It was also found that the hair treated according to the present disclosure felt more conditioned and smooth to the touch compared to the hair treated by shampoo alone. In addition, when alkoxysilane, APTES, was present in the inventive compositions, the hair felt better conditioned and smooth to the touch compared to the inventive composition that did not contain APTES.

In similar tests conducted on hair on the head (salon test), it was also observed that hair was effectively straightened when treated similarly according to the procedure above, but without the contacting the hair with the neutralizing composition.

Example III

Global Frizz (2-Dimensional)

General Procedure to Measure the Global Frizz of Wavy Hair:

This study employed three different test compositions which were applied onto hair swatches of natural brown wavy hair of approximately 2.7 g each (two hair swatches for each test composition).

The hair swatches were shampooed with an alkaline shampoo two times. The shampooed hair was then blow dried to 100% dry. The dried swatches were then treated with the test solutions (see below) according to a processing time of 20 minutes. The treated hair swatches were then straightened by passing a flat iron (400° F.) through the hair 3 times. The swatches were treated with the neutralizing composition which was allowed to remain on the hair for 5 minutes before shampooing and rinsing. The swatches were dried in ambient conditions then placed in controlled humidity (20% relative humidity (RH) overnight, then in 80% RH for 2 hours before taking measurements. Digital pictures of the swatches were taken. The pictures were then analyzed for global frizz values in $cm^2$ using an image analysis software and the data was then analyzed using a statistical software.

| Example | Test Compositions | Mean value of Global Frizz in cm2 |
|---|---|---|
| 5 | Shampoo only | 43.70 |
| 6 | 2% monoethanolamine + 1.975% Hydroxyethyl Urea + 10% Urea + 2% hexylene glycol + water (Q.S.) | 54.24 |
| 7 | 2% monoethanolamine + 1.975% Hydroxyethyl Urea + 10% Urea + 2% Aminopropyl Triethoxysilane + 2% hexylene glycol + water (Q.S.) | 2.08 |

The results showed that there was a significant reduction in the mean global frizz value when Example 7 was employed as compared to Examples 5 and 6.

Example IV Retention of curl reduction and reduction in volume of hair

The test was conducted on hair swatches of approximately 2.7 g each, made of natural brown wavy hair. Two hair swatches were used for each formulation example in the table below.

The hair swatches were shampooed with an alkaline shampoo two times. The shampooed hair was then blow dried to 100% dry. The dried swatches were then treated with the test solutions (see below) according to a processing time of 20 minutes. The treated hair swatches were then straightened by passing a flat iron (400° F.) through the hair 3 times. The swatches were treated with the neutralizing composition which was allowed to remain on the hair for 5 minutes before shampooing and rinsing. The swatches were dried in ambient conditions then placed in controlled humidity (20% relative humidity (RH) overnight, then in 80% RH for 2 hours before taking measurements. Digital pictures of the swatches were taken.

| Example | Test Compositions |
|---------|-------------------|
| 8 | Shampoo only (control) |
| 9 | 2% monoethanolamine + 10% Urea + 2% Aminopropyl Triethoxysilane + 2% hexylene glycol + water (Q.S.) |
| 10 | 2% monoethanolamine + 10% Urea + 5% Hydroxyethyl Urea + 2% Aminopropyl Triethoxysilane + 2% hexylene glycol + water (Q.S.) |

The swatches were subjected to several washing treatments with water: 1 wash, total of 2 washes, total of 4 washes and total of 6 washes. After each washing treatment, digital picture of the swatches were taken. The length and volume of the swatches were measured and % SE (straightening efficiency) values were calculated from the length measurements.

| Example | Average % SE Before washing | Average % SE 2 washes | Average % SE 4 washes | Average % SE 6 washes | Volume of hair* (cm) | Volume of hair** (cm) |
|---------|------|------|------|------|------|------|
| 8 | −37.5 | 26.00 | 51.11 | −149.76 | 2.3 | 1.5 |
| 9 | 83.01 | 49.58 | 72.54 | 26.63 | 1.2 | 1.2 |
| 10 | 93.75 | 120.18 | 82.52 | 32.30 | 1.4 | 1.4 |

*width of the hair swatch at the widest point along the length of the hair swatch
**width of the hair swatch at midpoint of the length of the hair swatch The data above shows that although the straightening efficiency decreased by the 6th wash, the swatches treated with formulation examples 9 and 10 still had better % SE values as compared to the swatches treated with the shampoo only which had a negative % SE value. This indicates that the hair treated according to the present disclosure did not revert back to its original curl pattern even after multiple washings. On the other hand, the swatch treated with the control, example 8, reverted back to a curlier pattern or configuration and became more frizzy/curly with subsequent washings. In addition, the straightening efficiency obtained from the treatment of hair with formulation example 10 containing hydroxyethyl urea was better than that of the hair treated by formulation example 9 or by shampoo only.

Example V

Color Retention

Experiments were done to compare the performance of the composition and method of the present disclosure with that of TGA (thioglycolic acid) based commercial products on artificially dyed hair.

The tests were done on approximately 1.3 g hair swatches made of platinum bleached hair which were previously colored with a red hair dye.

The hair swatches were shampooed with an alkaline shampoo two times. The shampooed hair swatches were blow dried to 100% dry. The dried swatches were then treated with the test compositions (see below) according to a processing time of 20 minutes. The treated hair swatches were then smoothened with simultaneous application of heat by passing a flat iron (400° F.) through the hair 3 times. The swatches were treated with the neutralizing composition which was allowed to remain on the hair for 5 minutes before shampooing and rinsing. The swatches were dried in ambient conditions before taking measurements. Colorimetric measurements and digital pictures of the swatches were taken.

The color of the hair swatches was measured using a Minolta CM2002 colorimeter in the L*a*b*system. In the L*a*b* system, the 3 parameters denote, respectively, the intensity or lightness of the color (L*), the value of the color on a green/red axis (a*) and the value of the color on a blue/yellow axis (b*). According to this system, the greater the value of L, the lighter or less intense the color is. Conversely, the lower the value of L, the darker or more intense the color is. Also, the greater value of a, the more intense the red color or shade is. Also, according to this system, the overall color change, ΔE, can be calculated from the ΔL, ΔA, and ΔB values. The greater the ΔE value, the greater the change in color.

| Example | Test compositions | L* | a* | b* |
|---------|-------------------|------|-------|-------|
| 11 | 2% monoethanolamine + 5% Hydroxyethyl Urea + 10% Urea + 1% Aminopropyl Triethoxysilane + 2% hexylene glycol + 20% Olive oil + water (Q.S.) | 31.88 | 29.30 | 14.95 |
| 12 | TGA based commercial product | 37.53 | 14.32 | 10.86 |

| | ΔL* | Δa* | Δb* | ΔE* |
|---|---|---|---|---|
| Difference of example 11 and example 12 | | | | |
| Data of example 11 - Data of example 12 | −5.65 | 14.98 | 4.09 | 16.52 |

From the results above, the higher a, Δa* and ΔE* values for the hair treated with Example 11 (inventive composition) indicate that the hair treated with Example 11 remained significantly more red compared to the hair treated with Example 12 (the TGA based commercial product) even after subjecting the hair to the straightening compositions/processes. These color differences on the hair swatches were also observed visually. This means that the hair treated according to the present disclosure retained its artificial color significantly better than the hair treated with the TGA based commercial product.

It is to be understood that the foregoing describes preferred embodiments of the invention and that modifications may be made therein without departing from the spirit or scope of the invention as set forth in the claims.

What is claimed is:

1. A process for reducing curl and/or frizziness of hair comprising:
    (a) providing a composition for reducing curl and/or frizziness of hair, said composition comprising, in a cosmetically acceptable carrier:
        (i) from about 1 to about 5% by weight of at least one non-hydroxide base chosen from monoethanolamine, triethanolamine, and ethylenediamine;
        (ii) from about 2 to about 20% by weight of two protein denaturants chosen from urea and hydroxyethylurea and present in a ratio by weight ranging from about 5:1 to about 2:1;
        (iii) from about 1 to about 10% by weight of amino propyl triethoxysilane
        (iv) optionally, at least one fatty substance;
    (b) contacting the hair with the composition in (a) to form treated hair;
    (c) optionally, rinsing the composition in (a) from the treated hair;

(d) optionally, contacting the treated hair with a conditioning agent;
(e) smoothing the treated hair using a combination of heat and means for physically smoothing hair to form smoothed hair;
(f) optionally, shampooing the smoothed hair; and
(g) rinsing the smoothed hair.

2. The process of claim 1, wherein (a)(iv) is chosen from lower alkanes, fatty alcohols, esters of fatty acids, esters of fatty alcohol, non-silicone oils, non-silicone waxes and silicones.

3. The process of claim 1, wherein (a)(iv) is employed in an amount of at least 10% by weight, based on the weight of the composition in (a).

4. The process of claim 1, wherein the composition in (a) is substantially free of formaldehyde-generating compounds.

5. The process of claim 1, wherein (b) is performed for less than about 60 minutes.

6. The process of claim 1, wherein the conditioning agent in (d) is chosen from plant oils, synthetic oils, silicones, esters, humectants, conditioning polymers, and cationic agents.

7. The process of claim 1, wherein (e) is performed using a hair dryer and means for physically smoothing hair chosen from a brush, an iron, a comb and combinations thereof.

8. The process of claim 1, wherein (e) is performed using a hot/flat iron at a temperature of at least about 70° C.

9. The process of claim 1, further comprising contacting the smoothed hair with a neutralizing composition after step (e) to form neutralized hair wherein the neutralizing composition has a pH of below about 7.

10. The process of claim 1, further comprising a pre-alkalizing step preceding step (a) wherein the hair is contacted with a pre-alkalizing composition having a pH of from about 8.0 to about 12.0 to form pre-alkalized hair.

11. The process of claim 10, wherein the pre-alkalizing composition is rinsed off the hair prior to step (a).

12. A composition for reducing curl and/or frizziness of hair, said composition comprising, in a cosmetically acceptable carrier:
(a) from about 1 to about 5% by weight of at least one non-hydroxide base chosen from monoethanolamine, triethanolamine, and ethylenediamine;
(b) from about 2 to about 20% by weight of two protein denaturants chosen from urea and hydroxyethylurea and present in a ratio by weight ranging from about 5:1 to about 2:1;
(c) from about 1 to about 10% by weight of amino propyl triethoxysilane;
(d) optionally of at least one fatty substance; and
(e) optionally, at least one auxiliary ingredient; all weights based on the total weight of the composition; and wherein the composition reduces the curl and/or frizziness of the hair.

13. The composition of claim 12, wherein (d) is chosen from lower alkanes, fatty alcohols, esters of fatty acids, esters of fatty alcohol, non-silicone oils, non-silicone waxes and silicones.

14. The composition of claim 12, wherein (d) is in an amount of at least 10% by weight, based on the weight of the composition.

15. The composition of claim 12, wherein the composition is substantially free of formaldehyde-generating compounds.

* * * * *